US006171789B1

(12) United States Patent
Johnson et al.

(10) Patent No.: US 6,171,789 B1
(45) Date of Patent: Jan. 9, 2001

(54) **INSERTION SEQUENCE FROM A VIRULENT ISOLATE OF *BURKHOLDERIA CEPACIA*, AND DIAGNOSTIC AND IDENTIFICATION PROCEDURES BASED THEREON**

(75) Inventors: Wendy M. Johnson, Kanata; Shaun D. Tyler, Gloucester; Kenneth R. Rozee, Halifax, all of (CA)

(73) Assignee: Her Majesty the Queen in right of Canada, as represented by the Minister of Health, Ottawa (CA)

( * ) Notice: Under 35 U.S.C. 154(b), the term of this patent shall be extended for 0 days.

(21) Appl. No.: 09/011,197

(22) PCT Filed: Aug. 16, 1996

(86) PCT No.: PCT/CA96/00550

§ 371 Date: Apr. 24, 1998

§ 102(e) Date: Apr. 24, 1998

(87) PCT Pub. No.: WO97/07237

PCT Pub. Date: Feb. 27, 1997

Related U.S. Application Data
(60) Provisional application No. 60/002,398.

(51) Int. Cl.[7] .............................. C12Q 1/68; C12P 19/34; C07H 21/02; C07H 21/04; C12N 15/00
(52) U.S. Cl. ........................... 435/6; 435/91.2; 536/23.1; 536/24.3; 935/76; 935/77; 935/78
(58) Field of Search .................... 536/23.1, 24.3; 435/6, 91.2; 935/76, 77, 78

(56) References Cited

U.S. PATENT DOCUMENTS

| | | | |
|---|---|---|---|
| 5,043,272 | * | 8/1991 | Hartley ................................. 435/91 |
| 5,650,321 | * | 7/1997 | Levy ................................. 435/252.3 |
| 5,677,127 | * | 10/1997 | Hogan et al. ........................... 435/6 |
| 5,731,150 | * | 3/1998 | Sandhu et al. .......................... 435/6 |

OTHER PUBLICATIONS

Ohta et al., J. of Bacteriology 172(1):236–242 (1990).*
Karpati et al., Molecular and Cellular Probes 10:397–403 (1996).*
O'Callaghan et al., J. of Clinical Pathology 47:222–226 (1994).*
Leff et al., Applied and Environmental Microbiology 61(4):1634–1636 (1995).*
Tyler et al., Clinical and Diagnostic Laboratory Immunology 2(4):448–453 (1995).*
EML Database entry Pcis402—Accession No. M64065; M33173; Jul. 14, 1995. Ferrante, A. et al.: "Nucleotide sequence of IS402 from *Pseudomonas cepacia*" XP002019968.
Journal of Infectious Diseases, vol. 172, No. 1, Jul. 1995, pp. 293–5, XP000609467 Cimolai N et al: "Insertional sequence for Bordetella Pertussis diagnostic polymerase chain reaction differentiate strains of *Pseudomonas cepacia*".
Journal of Bacteriology, vol. 177, No. 7, Feb. 1995, pp. 1030–8, XP000610505 Sajjan U et al: "Cable (cbl) type II pili of cystic fibrosis–associated *Burkholderia* (*Pseudomonas*) *cepacia*: nucleotide sequence of the cb1A pilin gene and novel morphology of the assembled appendage fibres".
Diagnostic Microbiology and Infectious Disease, vol. 20, No. 4, Dec. 1994, pp. 181–6, XP000610514, Rozee K et al: "Comparison by extended ribotyping of *Pseudomonas cepacia* isolated from cystic fibrosis patients with acute and chronic infections".
Journal of Clinical Microbiology, vol. 34, No. 7, Jul. 1996, pp. 1610–16, XP000610044 Tyler S.D. et al: "Identification of IS1356, a new insertion sequence, and its association with IS402 in epidemic strains of *Burkholderia cepacia* infecting cystic fibrosis patients".
Journal of Bateriology, vol. 176, No. 13, Jul. 1994, pp. 4034–42, XP000609638, Cheng, H.P., et al.: "Multiple replicons constituting the genome of *Pseudomonas cepacia* 17616".

* cited by examiner

Primary Examiner—Ethan Whisenant

(57) ABSTRACT

A novel IS (insertion sequence) element characteristic of a virulent isolate (ET12/cblA isolate) of *Burkholderia cepacia*. The IS element is a hybrid of two other IS elements commonly found in isolates of *B. cepacia*, namely IS402 [SEQ ID NO:2] and IS1356 [SEQ ID NO:3]. The IS hybrid IS element has the sequence shown in the Figure [SEQ ID NO:1]. The fact that the hybrid IS element is characteristic of the virulent isolate means that it can be used as an indicator of that isolate. Thus, the invention includes a method of testing for an ET12/cblA isolate of *B. cepacia* by testing a sample for the presence of the hybrid IS element, eg. by amplification of the IS element by PCR and identification of the amplified sequence.

6 Claims, 4 Drawing Sheets

Fig. 1a

```
GAGAGGTGGGGCGGCCTTGCTTGAGAAGCTTAGAGACGGTTTCAAAAAGGCCCGGTGGGGCTGTTAAC

TGGCCAAGCCGATCATTGACGACGAACCGTGGACATTGATCGAGCCGTTATTGCCGCCACCCAAGCGA
                                     IS402
                                                          |— Duplication —|
TTATGCCACGCAAACGCAAGGAAGAAGTGCCGGTAGAACCGGGCAAGGGCTTGAACCTGGACCCGGAA
    M  P  R  K  R  K  E  E  V  P  V  E  P  G  K  G  L  N  L  D  P  E
                                                                    IS1356
AATTCGCGGCCCTGAAGAAGGCGATATTCGAGCGCGCGCTGGGCGGCGAACTGACCCACCACCTGGGC
 Q  F  A  A  L  K  K  A  I  F  E  R  A  L  G  G  E  L  T  H  H  L  G
                                                                    IS1356
CCAGCCGTAAGCGCATCGCGACCGACGATGATCTGCTCGACATCGAGATTCCGCGCGACCGCGAAGGC
 T  S  R  K  R  I  A  T  D  D  D  L  L  D  I  E  I  P  R  D  R  E  G
                                                                    IS1356
ACGACAAGATCATTGCGATGTACGCACGCGGCATGAGCGTGCGGGAGATTCAGGGTTTCTTGCTGGAG
 D  D  K  I  I  A  M  Y  A  R  G  M  S  V  R  E  I  Q  G  F  L  L  E
                                                                    IS1356
TGATCGACGAAGTGCGCGAGTGGCAGCAGCGGCCGCTTGAGCCGATGTACCCGGTCGTGTTCTTCGAC
 V  I  D  E  V  R  E  W  Q  Q  R  P  L  E  P  M  Y  P  V  V  F  F  D
                                                                    IS1356
ACCTGGCGCTGGGCGTGCGCCGCGACGGCACACGCGACGTGCTGGGCCTCTGGATCGAGCAGACCGAG
 Y  L  A  L  G  V  R  R  D  G  T  R  D  V  L  G  L  W  I  E  Q  T  E
                                                                    IS1356
AGGACATTCTGATCGCCGTGGTCGACGGCCTGAAGGGCTTCCCCGGAAGCGATCAACACGGTGTTCCCG
 Q  D  I  L  I  A  V  V  D  G  L  K  G  F  P  E  A  I  N  T  V  F  P
                                                                    IS1356
TCGCCAGTTGGAAGGACCGGAAATCGGTCGCGGCGGCGCTCAAGGAAGTCTATCGGGCACCGTCGGCC
 F  A  S  W  K  D  R  K  S  V  A  A  A  L  K  E  V  Y  R  A  P  S  A
                                                                    IS1356
AATACCCTCCGATTGCCGCGCTCTGGCGCCGGGCCTGGGATCAGGTGATTCCGTTCTACGCCTTCGCG
 K  Y  P  P  I  A  A  L  W  R  R  A  W  D  Q  V  I  P  F  Y  A  F  A
                                                                    IS1356
TGCAGCTTCGAAAGATCATCAAGGCGCGCGGCCACTTCCCGTCGGACGAGGCCGCGCTCAAACTGATC
 M  Q  L  R  K  I  I  K  A  R  G  H  F  P  S  D  E  A  A  L  K  L  I
                                                                    IS1356
GGAAGAGCGCGATGACCCAGTTCGCGCTGCTTTACCCCGAACGATTCAACATTGGAATCTGAATCTCA
 W  K  S  A  M  T  Q  F  A  L  L  Y  P  E  R  F  N  I  G  I
                                                                    IS1356
AAAAACCCAGGCCGCCTGCCTGTTTCGAATCGCGCCGCGCTGACCGGCATCCTGTTCGTTCTCAAGAC
                                                                    IS402
ACTTGCTGGCGACGGCTACGCGATTGGCAGGCTGCGGGCGTATGGGATCGCCTGCACGAATTGCTGCT
```

Fig. 1b

```
TTGCGCGGCGAGCTGTTAACCTCAGGCATCGGAACAACTGAGACCGAGGAGA  120
          IS402
GCCTATCCGAACTTTTGTGTGTGAGGCATAAACTGATGGCCAAGGAGCCACG  240
              IS1356 IRL
                            IS1356
CTCATCAAGCAACTGGTGCCCGGAACGCTGGATCGGGCTTCGATCAACGAGC  360
 L  I  K  Q  L  V  P  G  T  L  D  R  A  S  I  N  E

TACGAGAAGGGCGATGCCAAGCCGGCGGGCCGCACGAACCATCGCAACGGCA  480
 Y  E  K  G  D  A  K  P  A  G  R  T  N  H  R  N  G

ACGTTCGATCCGGTGCTGATTGCCAAGGGCGAGCGACGCTTCACGGGCTTCG  600
 T  F  D  P  V  L  I  A  K  G  E  R  R  F  T  G  F

ATGTACGGCATCGAGGTGTCGCCGGAATTCATCAGCACGGTGACCGACGCCG  720
 M  Y  G  I  E  V  S  P  E  F  I  S  T  V  T  D  A

GCCTTGCGAGTCAAGATCCGCGACGAAGGCGTCGTGCGCAACAAGGCGATCT  840
 A  L  R  V  K  I  R  D  E  G  V  V  R  N  K  A  I

GGCGCCAAGTTCTGGCTGCGGGTGGTCAACGAGCTGAAGCTGCGCGGCGTGC  960
 G  A  K  F  W  L  R  V  V  N  E  L  K  L  R  G  V

GAAACGACGGTCCAGACCTGCATCGTGCATCTGATCCGGAACTCGCTGGACT  1080
 E  T  T  V  Q  T  C  I  V  H  L  I  R  N  S  L  D

GAAGCGGCCGCCGTGGCGCTGGACGCGTTCGATACGAGCCCGTGGGGTACGA  1200
 E  A  A  A  V  A  L  D  A  F  D  T  S  P  W  G  T

CCCGACATCCGGAAAATTGTATATACGACCAACGCGATCGAGTCGCTGCATA  1320
 P  D  I  R  K  I  V  Y  T  T  N  A  I  E  S  L  H

TGGCTGGCGCTGCGCAACGTCGTGGCCAAGTGGACCGGCTCTCGGCACGATT  1440
 W  L  A  L  R  N  V  V  A  K  W  T  G  S  R  H  D

ACCCGCCTCACACACGGAATTCCGGATACCTCCACCCAAGCCGCGGCGCGAG  1560
               IS1356 IRR          Duplication
                                    IS402
CGGACTGCGCTGGCGCGACCTGCCCGCCGAGATGGGCTGCGGCTCGGGCGTG  1680

TGCGAAGCTGCGAGCAGCAGACCAAATCGATTTCTCGCGAGCCGCAGTCGAT  1800
```

Fig. 1c

```
                                                                    IS402
TCCTCATCGATTCGCGCCGTTGGGGCGGGCCAAAAACTGGGCCAAACCCCACCGATCGCGCGCGACCA
                                                                    IS402
TCCTGACCGGCGCGAACGTTCACGATGTCACGCAGCTGCTGCCGCTGATCGATGCGATTCCGCCAATT
                                                                    IS402
GCGGTTACGACTCTGAGCGGCATCGACGCGCGTTGCGCGATCGCGGTATCGAGCCGGTTATCGCCAAG
                                                                    IS402
GCACGCATGCCTGGCTGCATCACTTCCGTCGTCTCCGCATTCGTTTCGAGCGCCGTGCAGACATTCAC
                                                                    IS402
GGGCCGACCAGTCTTTATGAAACCGTCTCTTAATTTGTCATATTGATCAGGACTATTTCTCATGGCAT
         IS402
```

Fig. 1d

```
GGTTCTAAGCACCACATCGTCACCGACGCCAATGGCACGCCGCTCGCGGCGA  1920

CGTGGGTTGCGCGGCCACCCACTGCAGAGACCGCGCGTGGTCTACGCCGATC  2040

CGCCGCACCGAACATGGCAGCGGCCTTGGAAAATATCGCTGGGTCGTTGAAC  2160

GGCGCGTTCCTCAAACTCGGTTGCTGCCTGATCTGCTGGAATACCCTTCGGC  2280

TGTTTCCTCCAGA  2361
```

INSERTION SEQUENCE FROM A VIRULENT ISOLATE OF *BURKHOLDERIA CEPACIA*, AND DIAGNOSTIC AND IDENTIFICATION PROCEDURES BASED THEREON

This application claims the priority right of provisional U.S. application Ser. No. 60/002,398 filed Aug. 17, 1995, and is a 371 of International Application No. PCT/CA96/00550, filed Aug. 16, 1996.

TECHNICAL FIELD

This invention relates to a novel hybrid insertion sequence found in virulent isolates of *Burkholderia cepacia*, and to methods of diagnosis and identification based on the hybrid insertion sequence. The invention also relates to uses of the hybrid insertion sequence obtained from the indicated isolates.

BACKGROUND ART

*Burkholderia cepacia* (formerly known as *Pseudomonas cepacia*) is an aerobic gram-negative bacillus commonly found throughout the environment and as a phytopathogen causing soft rot in onions (1) (the numbers in brackets used throught this disclosure refer to the articles identified in the section entitled "References" provided later in the specification). Over the past decade, however, strains have been encountered with increasing frequency which cause opportunistic infections in humans, most notably in cystic fibrosis (CF) patients leading to an increase in morbidity and mortality (12, 38). Among non-CF patients, extrapulmonary nosocomial infections in compromised individuals have more recently been reported (21).

Although the mechanism of virulence of *B. cepacia* has not been elucidated (20), isolates from CF patients have been shown to adhere to mucin (26) and buccal epithelial cells (27). There may also be a correlation between the source of *B. cepacia* isolates (e.g. environmental, CF-associated epidemic and non-epidemic isolates) and the particular class of pili expressed (9). In addition, epidemic foci in Canada have been found associated with a suite of enzyme alleles characterized as electrophore type 12 (ET12) (Johnson et al., 1994).

The implications of being colonized with *B. cepacia* are a growing concern in the CF community and markers of strain virulence are eagerly sought. Enhanced transmissibility and virulence appear to be strain dependent and epidemic lineages are being defined anecdotally and genetically (10, 13, 17, 33, 34, 35, 36). To date, studies have indicated cross-infection between patients (10, 17, 25, 31) and nosocomial acquisition (19) as important parameters of transmission.

In attempts to limit the spread of *B. cepacia*, many clinical centres now segregate colonized and non-colonized CF patients. This has proved to be successful but is limited by the social contacts between patients outside the hospital setting that is the norm for CF patient groups, especially adults (10, 17, 31), and by the likelihood that not all *B. cepacia* strains are virulent.

Many studies involving *B. cepacia* have focused on its truly extraordinary potential to metabolize a wide variety of organic compounds. It is currently thought that this metabolic versatility may, in part, be the result of the genomic complexity (24) comprising three chromosomes and a large plasmid with possibly a large number of insertion sequence (IS) elements (7, 15). IS elements have the ability to promote genomic rearrangement, recruit foreign genes and cause insertional gene activation. Indeed, most of the IS elements in *B. cepacia* have been identified by observing these features (16) that dramatically modify the activity of isolates (8). It is conceivable that they may act genetically to increase transmissibility and pathogenicity of certain strains of *B. cepacia*.

The inventors named in the present application originally identified the strains obtained by Govan et al. in 1993 and by themselves (13, 25), from the United Kingdom and Canada respectively, as having an identical enzyme electrophoretic allotype (ET12), the first direct evidence that the anecdotal association of Canadian *B. cepacia* strains currently endemic in Ontario and those causing an epidemic in the United Kingdom were the same.

However, while *B. cepacia* has recently been the subject of much research, not a great deal of information is available about why some strains are particularly virulent, and to what factors the difference in virulence can be attributed. In practice, there is a need for a simple diagnostic way of identifying particularly virulent isolates of *B. cepacia* so that carrier patients can be suitably treated and non-carrier patients can be protected.

DISCLOSURE OF THE INVENTION

A principal object of the present invention is to utilize a unique and newly discovered hybrid insertion sequence (IS402/IS1356—[SEQ ID NO:1]) for a variety of important diagnostic and identification purposes.

Another object of the invention is to provide a diagnostic method suitable for rapid and precise identification of virulent isolates of *B. cepacia* and possibly other bacteria.

Another object of the invention is to provide a test kit suitable for testing for a virulent strain of *B. cepacia*.

According to one aspect of the invention, there is provided an insertion element characteristic of a virulent strain ET12 of *Burkholderia cepacia*, said element being a hybrid of IS402 [SEQ ID NO:2] and IS1356 [SEQ ID NO:3].

The identified insertion element has the sequence of SEQ ID NO:1, but sequence variation may occur in nature and the present invention includes minor sequence changes that do not change the essential character of the parental sequence. It is highly improbable that any sequence variation of the IS402/IS1356 hybrid would be so extensive as to render the sequence biologically or genetically unrecognizable from the parental IS402/IS1356.

According to another aspect of the invention, there is provided a method of testing for the presence of ET12/cblA isolates of *Berkholderia cepacia* in a sample, comprising testing for a hybrid insertion sequence of IS402 [SEQ ID NO:2] and IS1356 [SEQ ID NO:3] characteristic of said isolates, and indicating the presence of the sequence if the sequence is detected.

The identification of the stated hybrid sequence normally indicates the presence of the virulent isolates of *B. cepacia* as indicated, but this hybrid insertion element may be passed to other organisms transferring virulence factors to such organisms. Accordingly, a positive indication of the presence of the hybrid sequence may indicate virulent isolates of organisms other than those of *B. cepacia*.

Any suitable method of testing for the presence of a known sequence may be used in the above method, for example PCR, ELISA-based methods, and other DNA sequence identification techniques. Such procedures are well known to persons skilled in the art and can be conducted relatively quickly and inexpensively compared to more conventional tests procedures for pathogenic organisms, such as metabolic discriminators and in vivo testing.

As an example, a method of testing involving PCR may involve: amplifying an insertion element sequence characteristic of strain ET12 of Berkholderia cepacia in a sample by polymerase chain reaction to form an amplified sequence, said insertion element being a hybrid of IS402 [SEQ ID NO:2] and IS1356 [SEQ ID NO:3]; and testing for the presence of said amplified sequence.

The basic techniques of the polymerase chain reaction are known, for example, from the following U.S. Pat. Nos. 4,683,202; 4,683,195; 4,683,188; and 5,075,216, among others. The disclosures of these patents are incorporated herein by reference.

The amplified sequence may be detected by any one of several known methods of identifying DNA segments. For example, this may be carried out by identifying the size (length of the DNA) using agarose gel electrophoresis, by designing labeled primers used for the PCR amplification, which primers are incorporated into the amplified sequences (labeling may be either radioactive or non-radioactive), or by designing a labeled (radioactive or non-radioactive) DNA probe for annealing with a known part of the amplified sequence, followed by Southern blot analysis or the like.

According to another aspect of the invention, there is provided a kit for the detection of virulent isolates of *B. cepacia*, comprising ingredients required for carrying out polymerase chain reaction and detection of a DNA sequence characteristic of the isolates, wherein the kit includes primers capable of amplifying, by polymerase chain reaction, a hybrid insertion sequence of IS402 [SEQ ID NO:2] and IS1356 [SEQ ID NO:3].

The present invention may be used, among other things, for the rapid identification of *Burkholderia cepacia* pathogens in patient (particularly CF patient) infections, for risk assessment in patient populations for remedial intervention, and regulatory evaluations of biotechnology products which are microorganisms, for rapid identification and evaluation of biological warfare agents, for assessment of environmentally released organisms and any human health and safety effects thereof.

BRIEF DESCRIPTION OF THE DRAWINGS

FIGS. 1a, 1b, 1c and 1d together shown the DNA sequence of Insertion Sequence IS402/IS1356, indicating the parts derived from IS402, the parts derived from IS1356, and various regions of sequence duplication. A peptide sequence [SEQ ID NO:4] corresponding to part of the nucleotide sequence is also shown in the Figures. FIGS. 1a and 1b, positioned side-by-side, form the first part of the DNA and nucleotide sequences, and FIGS. 1c and 1d, positioned side-by-side, form the second and final part of the sequences.

BEST MODES FOR CARRYING OUT THE INVENTION

The inventors of the present invention carried out a study to investigate the frequency of various insertion sequence (IS) elements in *B. cepacia* to determine if any relationship exists between the presence of particular IS elements and electrophoretic type (ET), ribotype (PT) or cable A pili (cblA) of various known isolates (strains).

During the course of the investigations, the inventors succeeded in identifying a previously unreported IS element which has been designated IS1356 [SEQ ID NO:3]. This sequence has a structure typical of insertion sequences in that it is terminated by inverted repeats and contains an open reading frame which spans virtually its entire length and codes for a putative transposase. An interesting feature of IS1356 is the high degree of similarity of the transposase to a variety of others identified on IS elements from a wide distribution of organisms. During the characterization of ISRm5, Laberge et al. (1995), observed that there appears to be a family of IS elements, of which IS1356 is now a member, which share a common ancestry even though the hosts of these IS elements are from highly divergent bacterial families.

Tests were carried out for IS1356 and several known IS elements, i.e. IS elements IS402 [SEQ ID NO:2], IS406, IS407, IS408 and a newly discovered IS1356 [SEQ ID NO:3], using the polymerase chain reaction (PCR) employing primers designed for these specific elements (see Table 1 below).

TABLE 1

Oligonucleotide primers used to detect the various IS elements and cblA pilin subunit gene in *Burkholderia cepacia.*

| TARGET GENE | | PRIMER SEQUENCES | | | | | | | SEQ ID NO: | AMPLICON SIZE (BP) |
|---|---|---|---|---|---|---|---|---|---|---|
| IS402 | A: | 5' - caa | ccg | aga | ctg | agg | aga | tg - 3' | 7 | 250 |
| | B: | 5' - gct | gct | tgc | caa | tcg | cgc | tc - 3' | 8 | |
| IS406 | A: | 5' - gac | ggt | ggg | tct | gac | gcc | at - 3' | 9 | 450 |
| | B: | 5' - aag | ccc | tga | gtc | cct | cgt | cg - 3' | 10 | |
| IS407 | A: | 5' - tca | tcg | ggt | ttc | tga | agg | aa - 3' | 11 | 750 |
| | B: | 5' - cgg | aag | cga | gct | gca | cgg | tc - 3' | 12 | |
| IS408 | A: | 5' - ttg | aag | gaa | gtc | ctg | cga | ct - 3' | 13 | 370 |
| | B: | 5' - tcq | act | tcg | ccc | aat | cct | tg - 3' | 14 | |
| IS1356 | A: | 5' - ggc | cct | gaa | gaa | ggc | gat | at - 3' | 5 | 327 |
| | B: | 5' - tcc | ggc | gac | acc | tcg | atg | cc - 3' | 6 | |
| cblA[1] | A: | 5' - cca | aag | gac | taa | ccc | a - 3' | | 15 | 610 |
| | B: | 5' - acg | cga | tgt | cca | tca | ca - 3' | | 16 | |

[1]Primers were first described by Sajjan, et al. (28)

It was found that there was no apparent link between the presence of the IS elements and the ET, RT or cblA genotype of the isolates, with one notable exception. The primers targeting IS402, in addition to detecting the expected IS element, also primed an additional amplicon of approximately 650 base pairs (bp) in some isolates. This anomaly was restricted to strains designated ET12 which is the ET of isolates documented to be highly transmissible in CF patients (Govan et al., 1993; Smith et al., 1993; Johnson et al., J.Clin.Microbiol. 32:924–930, 1994).

Sequence data revealed that the 650 bp amplicon consisted initially of the IS402 sequence but this was interupted after 154 bp and succeeded by that of IS1356.

DNA from thirty *P. cepacia* isolates collected by the DNA Core Facility, Laboratory Centre for Disease Control, HPB Building, Tunney's Pasture, Ottawa, Ontario, Canada, was screened with the IS402 primers and 18 additional isolates which produced the 650 bp amplicon were included with those previously described (Johnson et al., 1994). When subjected to electrophoretic typing, all 18 isolates were found to be ET12, so it appears that the hybrid insertion sequence is characteristic of ET12 isolates and also of those carrying the cblA gene. In addition, the site of insertion of the IS402/IS1356 element was identical in all of the isolates investigated, further supporting the clonal nature of this group of isolates.

The IS402/IS1356 hybrid was cloned and sequenced. The sequence determined in this way [SEQ ID NO:1] is shown in FIGS. 1a, 1b, 1c and 1d of the accompanying drawings. The hybrid consists of the insertion sequence IS402, which is identical to that previously reported (Ferrante et al., 1991) including the 3 base duplication (5'-tta- 3') at the insertion site. As noted above, the IS402 sequence is interrupted after 154 bases by IS1356 resulting in a 10 bp duplication at the insertion site. IS1356 is 1353 bp in length and terminates at both ends in imperfect inverted repeats. IRL is 27 bp in length and IRR is 29 bp with 7 mismatches over the common region. IS1356 contains one major open reading frame of 1260 bp which codes for a putative transposase. This transposase showed significant homologies to several others found in the Swiss-Prot 31 database with the most significant homologies to ISRm3 (Wheatcroft and Laberge, 1991) found in *Rhizobium meliloti* (59%) and to one found in *Corynebacterium diphtheriae* (Unpublished, accession: P35879) (49%).

The fact that hybrid IS element IS402/IS1356 is characteristic of isolate ET12/cblA, a strain of *B. cepacia* that has been found to be highly virulent and transmissible in CF patients, means that diagnostic tests can be designed to identify this strain and to distinguish it from other strains of *B. cepacia*, many of which are known to colonize the respiratory pathways of cystic fibrosis patients with no ill effects. The hybrid element can thus be used as a diagnostic marker and an identifiable complementary sequence may be developed to bind to this sequence, when present in a test isolate.

A suitable diagnostic test method may involve utilization of the polymerase chain reaction (PCR) to amplify the characteristic sequence of the virulent strain in a sample, together with identification of the amplified sequence. The primers used for the PCR in this case may be primers IS402-A [SEQ ID NO:7] and IS1356-B [SEQ ID NO:6] shown in Table 1, although other suitable primers may easily be devised by a person skilled in the art. Standard conditions may be used for the PCR and the target sequence may be identified in the normal ways, e.g. by gel electrophoresis and Southern blotting using a $^{32}$P-labeled probe or visible marker having a sequence complementary to a unique part of the hybrid IS402/IS1356 element. The resulting fragment mixture may then be subjected to exposure to photographic film. The presence of a visible band or a mark on a developed film indicates the presence of the hybrid IS element, and thus confirm the microorganism as an ET12/cblA isolate of *B. cepacia*.

Samples on which such a test may be performed include anything from a sputum sample to purified bacterial DNA.

To ensure that strain ET12 containing the hybrid IS of interest in the present invention will remain available, a sample of the strain was deposited at the American Type Culture Collection (ATCC) of 10801 University Blvd., Manassas, Va. 20110-2209, U.S.A. on Aug. 14, 1996 under the terms of the Budapest Treaty and has been awarded deposit number ATCC 55807. As noted, this sample contains the hybrid IS402/IS1356 sequence, which can be amplified, isolated and identified using the techniques described in this specification.

The following is an Example of the way in which the present invention may be put into practice. It should be noted that the invention is not limited to this Example.

EXAMPLE

DETECTION OF IS402/IS1356 USING WHOLE CELL PCR

The overall procedure for testing for the insertion element consists of three individual stages, namely sample preparation, PCR detection of the hybrid insertion element and detection of the PCR product (amplified sequences). This may be carried out as follows.

The following reagents are obtained.
Reagents
  Nucleotides
  100 mM dCTP (Sigma D-4913)
  100 mM dATP (Sigma D-4788)
  100 mM dTTP (Sigma T-9656)
  100 mM dGTP (Sigma D-5038)
  The contents of all the tubes are added to 24 ml ddH$_2$O, mixed well and stored at −20° C. Aliquots of 960 μl/tube are used.
Primers
  Primers specific to the hybrid sequence are prepared (e.g. primers IS402-A [SEQ ID NO:7] and IS1356-B [SEQ ID NO:6] shown in Table 1) and are stored in dehydrated form, kept at −20° C. and are reconstituted as needed, e.g. by adding 1250 μl ddH$_2$O to 5 O.D. primer and dissolving at room temperature for 30 minutes, and are stored at −20° C.
Tris Borate EDTA Buffer (TBE)
  0.089 M Tris
  0.089 M Boric Acid
  0.0025 M EDTA
This buffer may be purchased in a pre-packaged form from ICN (816202). One package is added to 4 l dH$_2$O and is dissolved for 30 minutes while mixing on magnetic stirrer. This is used as a running buffer for gel electrophoresis and to prepare agarose gels.
Gel Loading Buffer—PCR Dye
  0.25% bromophenol blue
  0.25% xylene cyanol
  15% (Ficoll type 400) in dH$_2$O
  The three ingredients are added together and mixed well and stored at room temperature.
100 bp or 123 bp DNA Ladder (Gibco BRL #15628-019—Trade Mark)
  120 μl DNA ladder (1 ug/1 μl )
  380 μl TE Buffer (pH 8.0)
  100 μl PCR Dye
  The three ingredients are added together and mixed well and stored at 4° C.

Agarose Gels

A 2% agarose gel is used to analyze PCR products. Add 2 g DNA grade agarose (BIO RAD 162-0126) to 100 ml TBE buffer, mix well and heat for 3 minutes (or until melted) on high in microwave, mixing every 30 seconds, let the agarose cool to 50° C. before pouring into gel molds, pour the agarose into molds (each one takes about 50 ml) and let the gels set for 20 minutes.

Ethidium Bromide

Prepare a stock solution of Ethidium Bromide (2 mg/ml), add 5 µg/ml EtBr to TBE buffer used for the agarose gel preparation and 5 µl EtBr to 100 ml TBE running buffer.

TAQ Polymerase

TAQ Polymerase may be purchased from Promega as a 10×Reaction Buffer containing 500 mM KCl, 100 mM Tris-HCl (pH 8.3), 15 mM $MgCl_2$, 1% Triton™ X-100. The enzyme and buffer are stored at −20° C.

PCR METHODS

Preparation of DNA template: Whole Cell DNA Inoculate a sample colony into 2 ml BHI broth, and incubate for 2 hours at 37° C. An amount of 5 µl of this preparation is used in the PCR reaction.

The use of whole cell DNA inoculates depends on having a culture of the test organism. The culture does not have to be pure as the presence of other organisms does not interfere with detecting a positive organisms in a mixture. To avoid the culturing procedure, an antibody specific for *B. cepacia* or even a generic antibody for all bacteria may be utilized. Antibodies targeting the peptidoglycogen component of the bacterial cell wall are currently available and may be used to purify and concentrate the bacteria present in a sample. Boiling the resulting product provides suitable material for use in the PCR stage of the procedure.

Preparation of Reaction Tubes:

The following are added together:

| Ingredient Concentration | Quantity | Final |
|---|---|---|
| dNTP Stock Mix (dATP, dCTP, dGTP, dTTP) | 320 µl | 200 µM of each |
| Primer Set Type 1(a) | 100 µl | 1 µM |
| Type 1(b) | 100 µl | 1 µM |
| 10 × Reaction Buffer | 200 µl | 1 X |
| dd$H_2O$ | 1070 µl | |

The master mix is kept at −20° C. and dispensed as required into 9600 style tubes.

Polymerase Chain Reaction:

TAQ is added to the PCR reaction mixture (0.5 µl/sample). The reaction mixture (45 µl) is dispensed into 9600 style tubes and 5 µl of culture (in BHI) is added into reaction tube (changing tips for each sample). The mixture is heated at 94° C. for 10 minutes and then 30 cycles each are run at:

94° C./30 s

60° C./30 s

72° C./30 s

At the end of the 30 cycles, the PCR tubes are incubated for 7 minutes at 72° C. for a final extension phase. This produces a PCR product.

Agarose Gel Electrophoresis:

Once the PCR product, it may be analyzed using agarose gel electrophoresis. A 2% agarose gel is used (prepared with TBE buffer) and TBE is also used as the running buffer. A 100 bp ladder is used on each gel as a standard and 10 pl of the PCR product +2.5 µl of loading buffer (this blue dye tracks the progress of DNA through the gel) is loaded into the well. Gels are run at 100 V for 1 hour (until loading dye is 1 cm from end of gel), stained with ethidium bromide and visualized under UV light. A photograph is taken to create a permanent record of the result. A positive sample will have a band at 592 base pairs.

A diagnostic test kit may be developed for carrying out the method indicated above. This test kit contains pre-mixed and aliquoted reagents so that all that would have to be added would be Taq polymerase, although this may be incorporated into the mixture as well). All that would additionally be required would be the sample to be tested.

Instead of employing agarose gel electrophoresis for detecting the PCR product, the well-known ELISA-based technology may be used instead. Detection by ELISA is particularly suited for test kits.

As a further alternative, a technology developed by Tm Technologies of Toronto, Ontario, Canada, based on work carried out by The Research Foundation of State University of New York, N.Y., USA, may be utilized. The technique allows for accurate detection of small amounts of specific DNA sequences without the need for thermal cycling.

In the following, the experimentation on which the present invention is based is presented in full detail.

MATERIALS AND METHODS

Bacterial strains, nucleic acid preparation, ribotyping and multilocus electrophoresis.

The collection of strains used in this investigation consisted of 99 isolates of *B. cepacia*, most of which were previously characterized for ET and RT (13). Strains were grown overnight on Columbia blood agar base (Quelabs, Montreal, Que.) at 37° C. in 5% $CO_2$ prior to nucleic acid (NA) extraction. The isolates were originally obtained as either isolates from CF patients or from nosocomial outbreaks and they were maintained in the culture collection of the Laboratory Centre for Disease Control, Ottawa, Canada. Two of the strains investigated were American Type Culture Collection (ATCC) reference strains of environmental origin (ATCC 17759 and ATCC 25416). Procedures for nucleic acid (NA) purification, ribotyping and multilocus enzyme electrophoresis (MLEE) were as previously described (13).

Oligonucleotide primers and PCR amplification.

Oligonucleotide primers designed to detect the various IS elements and the pilin subunit gene are summarized in Table 1 and are based on the published sequences for IS402 (6), IS406 and IS407 (41), IS408 (2) and cblA (36). Primers for the detection of IS1356 were designed based on sequence data acquired in this investigation. All primers were synthesized on a 392 DNA/RNA Synthesizer (Applied Biosystems, Foster City, Calif.) using standard phosphoramidite chemistry. Amplification was performed in a PE9600 (Perkin Elmer Cetus, Foster City, Calif.) thermocycler with PCR reaction mixtures containing 0.2 mg/ml NA, 200 mM dNTP, 1 mM of each primer in the pair, 50 U/ml Taq polymerase (Boehringer Mannheim, Laval, Que.,) and 1x reaction buffer supplied by the manufacturer. Thermocycling conditions consisted of an initial denaturation of 2 min. at 94° C. followed by 30 cycles of 30 sec. at 94° C., 30 sec. at 60° C. and 30 sec. at 72° C. Following amplification, samples were incubated at 72° C. for 10 min. and then cooled to 4° C. Amplicons were detected by electrophoresis in 2% agarose and staining with ethidium bromide (29).

Vectorette PCR was performed as previously described (23) using primer IS1356-A (Table 1) as the target primer. Vectorette libraries were constructed with NA from strain LCDC 92-498 (ET12, RT20) for BamHI, BclI, BglII, EcoRI, HindIII, NheI, SalI, SpeI, and XbaI. This isolate is a member of the group of strains implicated in the spread of *B. cepacia* ET12 between the UK and Canada (10, 13, 31). Amplification was performed as above using a two step thermocycling profile of 30 cycles of 94° C. for 30 sec. and 72° C. for 3 min. Reaction mixtures were analyzed on a 1% low melt agarose gel and the resulting amplicons were excised from the gel and purified using the Wizard PCR Prep Purification system (Promega, Madison Wis.).

Cloning and Sequencing of IS402/IS1356.

A bacteriophage library was constructed from the strain LCDC 92-498 using the ZAP™ Express Cloning Kit (Stratagene, La Jolla, Calif.). The probe was prepared by amplifying NA from strain LCDC 92-498 with the primers IS1356-A and IS1356-B (Table 1) in the presence of digoxigenin-11-uridine-5'-triphosphate. PCR conditions were identical to those used to detect the insertion sequence however the dNTP's were substituted with DIG™ Labeling Mix (Boehringer Mannheim). Positive clones were identified using the DIG DNA Detection Kit (Boehringer Mannheim) according to the manufacturers directions. After purification of the bacteriophage clones the phagemids were excised as directed in the ZAP™ Express Kit and plasmid DNA was purified using the Quiawell™ Plus Plasmid purification system (Quiagen, Chatsworth, Calif.) as recommended by the manufacturer.

Sequencing was performed on an ABI 373 automated DNA sequencer using the Prism Dye Terminator™ sequencing kit (Applied Biosystems). Sequencing primers were designed based on acquired data as required to complete the sequence. Sequence analysis was performed using the various programs supplied with PG/Gene™ (Intelligenetics, Mountain View, Calif.) and Lasergene™ (DNAStar, Madison, Wis.). Phylogenetic analysis was performed using PAUP 3.0 (37).

IS designation and GenBank accession number.

The IS1356 designation was from Dr. Esther M. Lederberg (Stanford University School of Medicine, Stanford, Calif.) under the auspices of the Plasmid Reference Centre Prefix Registry. The IS402/IS1356 sequence has been assigned GenBank accession no. U44828.

RESULTS

Frequency of targeted IS elements in B. cepacia.

The frequency of targeted IS elements in B. cepacia from environmental, nosocomial and CF sorces are recorded in Table 2.

mately 650 bp in some isolates. This anomaly was restricted to strains designated ET12 which is the ET of isolates documented to be highly transmissible in CF patients (10, 13, 31). Sequence data revealed that the 650 bp amplicon consisted initially of IS402 sequence but this was interrupted after 154 bp and succeeded by that of IS1356.

Cloning and characterization of IS402/IS1356.

Through the use of vectorette PCR an amplicon of approximately 1300 bp was obtained from the BclI library and was used for sequencing. The BglI and EcoRI libraries also produced amplicons but these were considerably smaller in size and were not investigated further. After sequencing of the amplicon further attempts at "gene walking" through the use of vectorette PCR proved unsuccessful due to the large number of unreasolvable amplicons obtained.

The IS402/IS1356 [SEQ ID NO:1] element consists of the insertion sequence IS402 [SEQ ID NO:2] reported by Ferrante et al., 1991, including the 3 base duplication (5'-tta-3') at the insertion site. Although certain sequence differences were detected between the IS402 previously reported and the one present in the hybrid these difference were not considered significant. The IS402 sequence is interrupted after 154 bases by IS1356 [SEQ ID NO:3] resulting in a 10 bp duplication at the insertion site. IS1356 is 1353 bp in length and terminates at either end by imperfect inverted repeats. IRL is 27 bp in length and IRR is 29 bp with 7 mismatches over the common region. IS1356 contains one major open reading frame of 1260 bp which codes for a putative transposase. This transposase showed significant homologies to several others found in the Swiss-Prot 31 database with the most significant homologies of 59% to ISRm3 found in Rhizobium meliloti (40) and 49% to an undesignated one found in Corynebacterium diphtheriae (22).

In order to determine if the IS402/IS1356 element had a conserved insertion site, primers were designed which would amplify either the 5'- or 3'- insertion sites and the

TABLE 2

Distribution of IS elements in isolates of B. cepacia.

| SOURCE | NO. OF ISOLATES | IS402 | IS406 | IS407 | IS408 | IS1356 | IS402/ IS1356 |
|---|---|---|---|---|---|---|---|
| Environmental | 2 | 0 (0.0%) | 0 (0.0%) | 0 (0.0%) | 0 (0.0%) | 1 (50.0%) | 0 (0.0%) |
| Nosocomial | 15 | 10 (66.7%) | 7 (46.7%) | 2 (13.3%) | 12 (80.0%) | 4 (26.7%) | 0 (0.0%) |
| Cystic Fibrosis | 82 | 58 (70.7%) | 15 (18.3%) | 46 (56.1%) | 41 (50.0%) | 66 (80.5%) | 36 (43.9%) |
| Total | 99 | 68 (68.7%) | 22 (22.2%) | 48 (48.5%) | 53 (53.5%) | 71 (71.7%) | 36 (36.4%) |

Overall, IS402 was found in 68.7% of the isolates, IS406 in 22.2%, IS407 in 48.5%, IS408 in 53.5% and IS1356 in 71.7%. In addition to these IS elements, primer sets were also designed to amplify IS401 (2) but no amplicons were detected in this collection of isolates (data not shown). There were no apparent linkages between the presence of these IS elements with ET or PT with one notable exception. The primers targeting IS402, in addition to detecting the IS element, also primed an additional amplicon of approxiresulting amplicons were sequenced (data not shown). All isolates in which the IS402/IS1356 hybrid IS element was detected yielded an amplicon of the predicted size with a sequence identical to that originally identified.

Distribution of targeted IS elements and cblA pilin subunit genes among several B. cepacia electrophoretic types.

Table 3 summarizes the distribution of IS elements and cblA pilin subunit genes in the inventors' collection of 99 strains representative of 20 electrophoretic types.

TABLE 3

Distribution of targeted genes in *B. cepacia* strains representing 20 electrophoretic types.

| ELECTROPHORETIC TYPE | NO. OF ISOLATES TESTED | SOURCE[1] | IS402 | IS406 | 15407 | IS408 | IS1356 | IS402/IS1356 | CBLA |
|---|---|---|---|---|---|---|---|---|---|
| 1 | 1 | CF | 1 | 0 | 1 | 1 | 1 | 0 | 0 |
| 2 | 1 | CF | 1 | 0 | 1 | 0 | 0 | 0 | 0 |
| 3 | 1 | NS | 1 | 0 | 0 | 1 | 0 | 0 | 0 |
| 4 | 2 | CF | 0 | 0 | 0 | 0 | 1 | 0 | 0 |
| 5 | 1 | CF | 0 | 0 | 1 | 0 | 0 | 0 | 0 |
| 6 | 3 | CF | 0 | 0 | 0 | 0 | 2 | 0 | 0 |
| 7 | 1 | CF | 0 | 0 | 0 | 0 | 0 | 0 | 0 |
| 8 | 2 | NS | 2 | 1 | 2 | 1 | 0 | 0 | 0 |
| 9 | 1 | ENV | 0 | 0 | 0 | 0 | 0 | 0 | 0 |
| 10 | 1 | NS | 0 | 0 | 0 | 1 | 0 | 0 | 0 |
| 11 | 5 | NS | 1 | 3 | 0 | 4 | 2 | 0 | 0 |
| 12[2] | 36 | CF | 37 | 10 | 37 | 32 | 38 | 36 | 38 |
| 13[3] | 1 | CF | 1 | 0 | 1 | 0 | 1 | 0 | 1 |
| 14 | 1 | CF | 0 | 0 | 1 | 0 | 1 | 0 | 0 |
| 15 | 1 | NS | 1 | 0 | 0 | 1 | 1 | 0 | 0 |
| 16 | 18 | CF | 9 | 2 | 2 | 1 | 18 | 0 | 0 |
| 17 | 12 | CF | 10 | 2 | 2 | 7 | 5 | 0 | 0 |
| 18 | 4 | NS | 4 | 4 | 0 | 4 | 0 | 0 | 0 |
| 19 | 1 | ENV | 0 | 0 | 0 | 0 | 1 | 0 | 0 |
| 20 | 4 | CF | 0 | 0 | 0 | 0 | 0 | 0 | 0 |

[1] CF = cystic fibrosis patient; ENV = environmental; NS = nosocomial
[2] Epidemic transatlantic clone (Canada and the United Kingdom)
[3] Isolate from a Canadian cystic fibrosis patient in a province remote from Ontario and with no known epidemic.

When IS1356 was detected in strains, the primers did not permit discrimination between IS elements found as the hybrid and IS1356 located at other sites. The initial identification of the IS402/IS1356 element was accomplished by observing the 650 bp band obtained with the IS402 primer set; however, in these strains successful amplification of the target was difficult to reproduce so the presence of the hybrid was confirmed by screening all isolates with the IS402-A and IS1356-B primers to obtain a 592 bp amplicon (data not shown).

Two of the ET12 isolates studied were found to lack the IS402/IS1356 element. One of these isolates was found to possess all of the other IS elements investigated except IS406 and the other possessed IS408 and IS1356. Neither of these two ET12 isolates lacking the hybrid element were clearly associated with the epidemic in that one is a reference strain used many years ago to establish the serotyping scheme for *B. cepacia* (18) and the other came from a cystic fibrosis patient resident in a remote area of Northern Ontario with no known association with areas of the provincial epidemic in the south. The cblA pilin subunit gene was found in all ET12 isolates tested and one strain of ET13 from an adult cystic fibrosis patient in a province remote from Ontario. There is no documented evidence of epidemic association or spread of this single ET13 isolate which differs in only one esterase allele from ET12 and which is IS402/IS1356 negative (Table 3). The cblA amplicon from this isolate was subjected to sequence analysis and found to be identical to that in the ET12 isolates (data not shown).

REFERENCES

1. Burkholder, W. H. 1950. Sour skin, a bacterial rot of onion bulbs. Phytopathology 40: 115.
2. Byrne, A. M., and Lessie, T. G. 1994. Characteristics of IS401, a new member of the IS3 family inplicated in plasmid rearrangements in *Pseudomonas cepacia*. Plasmid 31: 138–147.
3. Byrne, M. E., Rouch, D. A., and Skurray, R. A. 1989. Nucleotide sequence analysis of IS256 from the *Staphylococcus aureus* gentamycin-tobramycin-kanamycin-resistance transposon Tn4001. Gene 81: 361–367.
4. Collins, D. M., and Stephens, D. M. 1991. Identification of an insertion sequence, IS1081, in *Mycobacterium bovis*. FEMS Microbiol. Lett. 83: 11–16.
5. Dodd, H. M., Horn, N., and Gasson, M. J. 1994. Characterization of IS905, a new multicopy insertion sequence identified in lactococci. J. Bacteriol. 176: 3393–3396.
6. Ferrante, A. A., and Lessie, T. G. 1991. Nucleotide sequence of IS402 from *Pseudomonas cepacia*. Gene 102: 143–144.
7. Gaffney, T. D., and Lessie, T. G. 1986. Insertion-sequence-dependent rearrangements of *Pseudomonas cepacia* plasmid pTGL1. J. Bacteriol. 169: 224–230.
8. Galas, D. J., and Chandler, M. 1989. Bacterial insertion sequences. In Mobile DNA. Berg, D. E. and Howe, M. M., (eds). Washington DC: American Society for Microbiology. pp. 109–162.
9. Goldstein, R., Sun, L., Jiang, R., Sajjan, U., Forstner, J. F., and Campanelli, C. 1995. Structurally variant classes of pilus appendage fibers coexpressed from *Burkholderia* (Pseudomonas) *cepacia*. J. Bacteriol. 177. 1039–1052.
10. Govan, J. R. W., Brown, P. H., Maddison, J., Doherty, C. J., Nelson, J. W., Dodd, M., Greening, A. P., and Webb, A. K. 1993. Evidence for transmission of *Pseudomonas cepacia* by social contact in cystic fibrosis. Lancet 342: 15–19.
11. Guedon, G., Bourgoin, F., Pebay, M., Roussel, Y., Colmin, C. and Decaris, B. 1995. Characterization and distribution of two insertion sequences, IS1191 and iso-IS981 in *Streptococcus thermophilus*: does intergeneric transfer of insertion sequences occur in lactic acid bacteria co-cultures? Mol. Microbiol. 16: 69–78.
12. Isles, A., Maclusky, I., Corey, M., Gold, R., Prober, C., Fleming, P., and Levison, H. 1984. *Pseudomonas cepacia* infection in cystic fibrosis: an emerging problem. J. Pediatr. 104: 206–210.
13. Johnson, W. M., Tyler, S. D., and Rozee, K. R. 1994. Linkage analysis of geographic and clinical clusters in

*Pseudomonas cepacia* infections by multilocus enzyme electrophoresis and ribotyping. J. Clin. Microbiol. 32: 924–930.
14. Laberge, S., Middleton, A. T., and Wheatcroft, R. 1995. Characterization, nucleotide sequence, conserved genomic locations of insertion sequence ISRm5 in *Rhizobium meliloti*. J. Bacteriol. 177: 3133–3142.
15. Lessie, T. G., and Gaffney, T. 1986. Catabolic potential of *Pseudomonas cepacia*. In The bacteria, vol. 10, The Biology of Pseudomonas. Sokatch, J. R., and Ornston, L. N., (eds). Orlando, Fla.: Academic Press, Inc. pp. 439–481.
16. Lessie, T. C., Wood, M. S., Byrne, A., and Ferrante, A. 1990. Transposable gene-activating elements in *Pseudomonas cepacia*. In Pseudomonas: biotransformations, pathogenesis, and evolving biotechnology. Silver, S., Chakrabarty, A. M., Iglewski, B., and Kaplan, S. (eds) Washington, D.C.: American Society for Microbiology. pp. 279–291.
17. LiPuma, J. J., Dasen, S. E., Nielson, D. W., Stern, R. C., and Stull, T. L. 1990. Person-to-person transmission of *Pseudomonas cepacia* between patients with cystic fibrosis. Lancet 336: 1094–1096.
18. McKevitt, A. L., Retzer, M. D. and Woods, D. E. 1989. Development and use of a serotyping scheme for *Pseudomonas cepacia*. Serodiagn. Immunother. 1: 177–184.
19. Nelson, J. W., Doherty, C. J., Brown, P. H., Greening, A. P., Kaufman, M. E., and Govan, J. R. W. 1991. *Pseudomonas cepacia* in inpatients with cystic fibrosis. Lancet 338: 1525
20. Nelson, J. W., Butler, S. L., Krieg, D., and Govan, J. R. W. 1994. Virulence factors of *Burkholderia cepacia*. FEMS Immun. Med. Microbiol. 8: 89–98.
21. Rabkin, C. S., Jarvis, W. R., Anderson, R. L., Govan, J., Klinger, J., LiPuma, J., Martone, W. J., Monteil, H., Richard, C., Shigeta, S., Sosa, A., Stull, T., Swenson, J., and Woods, D. 1989. *Pseudonomas cepacia* typing systems: collaborative study to assess their potential in epidemiologic investigations. Rev. Infect. Dis. 11: 600–607.
22. Rappuoli, R., Perugini, M., and Ratti, G. 1987. DNA element of *Corynebacterium diphtheriae* with properties of an insertion sequence and usefulness for epidemiological studies. J. Bacteriol. 169:308–312.
23. Riley, J., Butler, R., Ogilvie, D., Finniear, R., Jenner, D., Powell, S., Anand, R., Smith, J. C., and Markham, A. F. 1990. A novel, rapid method for the isolation of terminal sequences from yeast artificial chromosome (YAC) clones. Nucleic Acids Research 18: 2887–2890.
24. Rodley, P., Romling, U., and Tümmler, B. 1995. A physical genome map of *Berkholderia cepacia* type strain. Mol. Microbiol. 17: 57–67.
25. Rozee, K., Haase, D., MacDonald, N., and Johnson, W. 1994. Comparison by extended ribotyping of *Pseudomonas cepacia* isolates from cystic fibrosis patients with acute and chronic infections. Diag. Microbiol. Infect. Dis. 20: 181–186.
26. Sajjan, U. S., and Forstner, J. F. 1992. Identification of the mucin-binding adhesin of *Pseudomonas cepacia* isolated from patients with cystic fibrosis. Infect. Immun. 60:1434–1440.
27. Sajjan, U. S., and Forstner, J. F. 1993. Pole of a 22-kilodalton pilin protein in binding of *Pseudomonas cepacia* to buccal epithelial cells. Infect. Immun. 61:3157–3163.
28. Sajjan, U. S, Sun, L., Goldstein, R., and Forstner, J. F. 1995. Cable (Cbl) type II pili of cystic fibrosis-associated *Burkholderia* (Pseudomonas) *cepacia*: Nucleotide sequence of the cblA major subunit pilin gene and novel morphology of the assembled appendage fibers. J. Bacterial. 177:1030–1038.
29. Sambrook, J., Fritsch, E. F., and Maniatis, T. 1989. Molecular cloning: A laboratory manual, 2nd ed. Cold Spring Harbor Laboratory, Cold Spring Harbor, N.Y.
30. Scordilis, G. E., Ree, H., and Lessie, T. G. 1987. Identification of transposable elements which activate gene expression in *Pseudomonas cepacia*. J. Bacteriol. 169: 8–13.
31. Smith, D. L., Gumery, L. B., Smith, E. G., Stableforth, D. E., Kaufmann, M. E., and Pitt, T. L. 1993. Epidemic of *Pseudomonas cepacia* in an adult cystic fibrosis unit: evidence of person-to-person transmission. J. Clin. Microbial. 31: 3017–3022.
32. Soby, S., Kirkpatrick, B., and Kosuge, T. 1993. Characterization of an insertion sequence (IS53) located within IS51 on the iaa-containing plasmid of *Pseudomonas syringae* pv. *savastanoi*. Plasmid 29:135–141.
33. Steinbach, S., Sun, S., Jiang, R.-Z., Flume, P., Gilligan, P., Egan, T., and Goldstein, R. 1994. Transmissibility of *Pseudomonas cepacia* infection in clinic patients and lung-transplant recipients with cystic fibrosis. N. Engl. J. Med. 331: 981–987.
34. Sun, L., Jiang, R., Steinbach, S., Gilligan, P., Forstner, J., Flume, P., and Goldstein, R. 1993. Epidemiology of *P. cepacia* infection at the molecular genetic level. II. Evidence for variable transmissibility. Pediatr. Pulmonol. S9: A214.
35. Sun, L., Jiang, R., Steinbach, S., and Goldstein, R. 1993. Epidemiology of *P. cepacia* infection at the molecular genetic level. III. Genetic analysis of highly virulent strains. Pediatr. Pulmonol. S9: A215.
36. Sun, L., Jiang, R., Steinbach, S., Holmes, A., Campanelli, C., Forstner, J., Sajjan, U., Tan, Y., Riley, M., and Goldstein, R. 1995. The emergence of a highly transmissible lineage of $cbl^+$ *Pseudomonas* (Burkholderia) *cepacia* causing CF centre epidemics in North America and Britain. Nature Med. 1: 661–666.
37. Swofford, D. L. 1993. PAUP: Phylogenetic Analysis Using Parsimony, version 3.0. Computer program distributed by the Illinois Natural History Survey, Champaign.
38. Tablan, O. C., Chorba, T. L., Schidlow, D. V., White, J. W., Hardy, K. A., Gilligan, P. H. et al. 1985. *Pseudomonas cepacia* colonization in patients with cystic fibrosis: risk factors and clinical outcome. J. Pediatr. 107: 382–387.
39. Tailliez, P., Ehrlich, S. D., and Chopin, M.-C. 1994. Characterization of IS1201, an insertion sequence isolated from Lactobacillus helveticus. Gene 145: 75–79.
40. Wheatcroft, R., and Laberge, S. 1991. Identification and nucleotide sequence of *Rhizobium meliloti* insertion sequence ISRm3: similarity between the putative transposase encoded by ISRm3 and those encoded by *Staphylococcus aureus* IS256 and *Thiobacillus ferrooxidans* IST2. J. Bacteriol. 173: 2530–2538.
41. Wood, M. S., Byrne, A., and Lessie, T. G. 1991. IS406 and IS407, two gene-activating insertion sequences from *Pseudomonas cepacia*. Gene 105: 101–105.

The disclosures of all of the above references are specifically incorporated herein by reference.

What is claimed is:

1. An isolated and purified insertion element characteristic of the ET12 strain of *Burkholderia cepacia* which insertion element consists of SEQ ID NO:1 or a minor variant thereof not rendering the sequence biologically or genetically unrecognizable from SEQ ID NO:1.

2. A method of testing for a virulent isolate of *Berkholderia cepacia* in a sample which comprises:
   a) testing said sample for the presence or absence of an insertion element which insertion element consists of SEQ ID NO:1 or a minor variant thereof not rendering the sequence biologically or genetically unrecognizable from SEQ ID NO:1;
   b) providing an indication of the presence or absence of said insertion element thereby indicating the presence or absence of a virulent isolate of *Berkholderia cepacia* in said sample.

3. The method of claim 2, wherein said sequence is tested for by a method based on polymerase chain reaction or ELISA.

4. The method of claim 3, comprising amplifying said insertion element sequence by polymerase chain reaction to form an amplified sequence, and indicating the presence of said sequence.

5. The method of claim 4, wherein the presence of said amplified sequence is indicated by identifying the size (DNA length) of the amplified sequence, by gel elecrophoresis, by means of labeled primers used for said polymerase chain reaction, which primers are incorporated into the amplified sequences, or by means of a labeled DNA probe for annealing with a unique part of the amplified sequence followed by Southern blot analysis.

6. A diagnostic test kit for detecting a virulent isolate of *Berkholderia cepacia* in a sample which comprises:
   a) reagents required to carry out PCR;
   b) primers capable of amplifying by PCR a hybrid insertion sequence consisting of SEQ ID NO:1 or a unique portion thereof;
   c) a positive control nucleic acid sequence which sequence comprises an isolated and purified insertion element characteristic of the ET12 strain of *Burkholderia cepacia* which insertion element consists of SEQ ID NO:1 or a minor variant thereof not rendering the sequence biologically or genetically unrecognizable from SEQ ID NO:1.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
       (A) LENGTH: 2361 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Burkholderia cepacia
       (C) INDIVIDUAL ISOLATE: ET12/cblA (xi) SEQUENCE DESCRIPTION: SEQ ID NO: 1:

```
GAGAGGTGGG GCGGCCTTGC TTGAGAAGCT TAGAGACGGT TTCAAAAAGG CCCGGTGGGG      60
CTGTTAACTT GCGCGGCGAG CTGTTAACCT CAGGCATCGG AACAACTGAG ACCGAGGAGA     120
TGGCCAAGCC GATCATTGAC GACGAACCGT GGACATTGAT CGAGCCGTTA TTGCCGCCAC     180
CCAAGCGAGC CTATCCGAAC TTTTGTGTGT GAGGCATAAA CTGATGGCCA AGGAGCCACG     240
TTATGCCACG CAAACGCAAG GAAGAAGTGC CGGTAGAACC GGGCAAGGGC TTGAACCTGG     300
ACCCGGAACT CATCAAGCAA CTGGTGCCCG AACGCTGGA TCGGGCTTCG ATCAACGAGC      360
AATTCGCGGC CCTGAAGAAG GCGATATTCG AGCGCGCGCT GGGCGGCGAA CTGACCCACC     420
ACCTGGGCTA CGAGAAGGGC GATGCCAAGC CGGCGGGCCG CACGAACCAT CGCAACGGCA     480
CCAGCCGTAA GCGCATCGCG ACCGACGATG ATCTGCTCGA CATCGAGATT CCGCGCGACC     540
GCGAAGGCAC GTTCGATCCG GTGCTGATTG CCAAGGGCGA GCGACGCTTC ACGGGCTTCG     600
ACGACAAGAT CATTGCGATG TACGCACGCG GCATGAGCGT GCGGGAGATT CAGGGTTTCT     660
TGCTGGAGAT GTACGGCATC GAGGTGTCGC CGGAATTCAT CAGCACGGTG ACCGACGCCG     720
TGATCGACGA AGTGCGCGAG TGGCAGCAGC GGCCGCTTGA GCCGATGTAC CCGGTCGTGT     780
TCTTCGACGC CTTGCGAGTC AAGATCCGCG ACGAAGGCGT CGTGCGCAAC AAGGCGATCT     840
ACCTGGCGCT GGGCGTGCGC CGCGACGGCA CACGCGACGT GCTGGGCCTC TGGATCGAGC     900
AGACCGAGGG CGCCAAGTTC TGGCTGCGGG TGGTCAACGA GCTGAAGCTG CGCGGCGTGC     960
AGGACATTCT GATCGCCGTG GTCGACGGCC TGAAGGGCTT CCCGGAAGCG ATCAACACGG    1020
TGTTCCCGGA AACGACGGTC CAGACCTGCA TCGTGCATCT GATCCGGAAC TCGCTGGACT    1080
TCGCCAGTTG GAAGGACCGG AAATCGGTCG CGGCGGCGCT CAAGGAAGTC TATCGGGCAC    1140
CGTCGGCCGA AGCGGCCGCC GTGGCGCTGG ACGCGTTCGA TACGAGCCCG TGGGGTACGA    1200
AATACCCTCC GATTGCCGCG CTCTGGCGCC GGGCCTGGGA TCAGGTGATT CCGTTCTACG    1260
CCTTCGCGCC CGACATCCGG AAAATTGTAT ATACGACCAA CGCGATCGAG TCGCTGCATA    1320
TGCAGCTTCG AAAGATCATC AAGGCGCGCG GCCACTTCCC GTCGGACGAG GCCGCGCTCA    1380
AACTGATCTG GCTGGCGCTG CGCAACGTCG TGGCCAAGTG GACCGGCTCT CGGCACGATT    1440
GGAAGAGCGC GATGACCCAG TTCGCGCTGC TTTACCCCGA ACGATTCAAC ATTGGAATCT    1500
GAATCTCAAC CCGCCTCACA CACGGAATTC CGGATACCTC CACCCAAGCC GCGGCGCGAG    1560
```

-continued

```
AAAAACCCAG GCCGCCTGCC TGTTTCGAAT CGCGCCGCGC TGACCGGCAT CCTGTTCGTT    1620

CTCAAGACCG GACTGCGCTG GCGCGACCTG CCCGCCGAGA TGGGCTGCGG CTCGGGCGTG    1680

ACTTGCTGGC GACGGCTACG CGATTGGCAG GCTGCGGGCG TATGGGATCG CCTGCACGAA    1740

TTGCTGCTTG CGAAGCTGCG AGCAGCAGAC CAAATCGATT TCTCGCGAGC CGCAGTCGAT    1800

TCCTCATCGA TTCGCGCCGT TGGGGCGGGC CAAAAACTGG GCCAAACCCC ACCGATCGCG    1860

CGCGACCAGG TTCTAAGCAC CACATCGTCA CCGACGCCAA TGGCACGCCG CTCGCGGCGA    1920

TCCTGACCGG CGCGAACGTT CACGATGTCA CGCAGCTGCT GCCGCTGATC GATGCGATTC    1980

CGCCAATTCG TGGGTTGCGC GGCCACCCAC TGCAGAGACC GCGCGTGGTC TACGCCGATC    2040

GCGGTTACGA CTCTGAGCGG CATCGACGCG CGTTGCGCGA TCGCGGTATC GAGCCGGTTA    2100

TCGCCAAGCG CCGCACCGAA CATGGCAGCG GCCTTGGAAA ATATCGCTGG GTCGTTGAAC    2160

GCACGCATGC CTGGCTGCAT CACTTCCGTC GTCTCCGCAT TCGTTTCGAG CGCCGTGCAG    2220

ACATTCACGG CGCGTTCCTC AAACTCGGTT GCTGCCTGAT CTGCTGGAAT ACCCTTCGGC    2280

GGGCCGACCA GTCTTTATGA AACCGTCTCT TAATTTGTCA TATTGATCAG GACTATTTCT    2340

CATGGCATTG TTTCCTCCAG A                                              2361
```

(2) INFORMATION FOR SEQ ID NO: 2:

(i) SEQUENCE CHARACTERISTICS:
       (A) LENGTH: 1039 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 2:

```
TGAAGACGAA AGGGCCTCGT GATACGCTTA GAGACGGTTT CAAAAAGGCC CCGTGGGGCT     60

GTTAACTTTC GCGGTGAGCT GTTAACCTCA GGCATCGGAA CAACCGAGAC TGAGGAGATG    120

GCCAAGCCGA TCATCGACGA TGAATTGTGG ACACTGATCG AGCCGTTACT GCCGCCACCC    180

AAGCCGCGGC GCGAGAAGAA CCCGGGCCGC CTGCCTGTTT CGAATCGCGC CGCGCTGACC    240

GGCATCCTGT TCGTTCTCAA GACCGGACTA CGCTGGCGCG ACCTGCCGGC CGAGATGGGA    300

TGCGGCTCGG GCGTGACATG TTGGCGCCGG CTGCGCGATT GGCAAGCAGC CGGTGTCTGG    360

GATCGCTTGC ACGAGCTACT GCTCGCAAAG CTGCGCGCAG CGGACCAGAT CGACTTCTCA    420

CGAGCCGCCG TCGATTCATC ATCGATTCGC GCCGTTGGGG CAGGCCAAAA ACTGGGCCAA    480

ACCCCACCGA TCGCGCGCGA CCCGGTTCCA AGCACCACAT CGTCACCGAC GCCAACGGTA    540

CGCCGCTCGC CGCGATCCTG ACCGGCGCGA ACGTCAACGA CGTCACGCAA TTGCTGCCGC    600

TGATCGACGC GATTCCGCCG ATCCGCGGAT TGCGTGGCCA CCCATTGCAG CGGCCGCGTG    660

TGGTCTACGC GGATCGCGGT TACGACTCCG AGCGACATCG GCGCGCGTTG CGCGATCGCG    720

GTATCGAGCC AGTGATCGCC AAGCGCCGTA CCGAACATGG CAGCGGCCTT GGCAAATATC    780

GCTGGGTCGT CGAACGCACG CATGCCTGGC TGCATCACTT CCGTCGTCTC CGTATTCGTT    840

TCGAGCGCCG TGCAGACATT CACGGCGCGT TCCTCAAACT CGGTTGCTGT CTGATCTGCT    900
```

```
GGAATACCCT TCGGCGGGCC GATCAGTCTT TATGAAACCG TCTCTTATTT TTATAGGTTA      960

ATGTCATGAT AATAATGGTT TCTTAGACGT CAGGTGGCAC TTTTCGGGGA AATGTGCGCG     1020

GAACCCCTAT TGTTTATT                                                   1039
```

(2) INFORMATION FOR SEQ ID NO: 3:

(i) SEQUENCE CHARACTERISTICS:
        (A) LENGTH: 1353 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 3:

```
GAGCCTATCC GAACTTTTGT GTGTGAGGCA TAAACTGATG GCCAAGGAGC CACGTTATGC       60

CACGCAAACG CAAGGAAGAA GTGCCGGTAG AACCGGGCAA GGGCTTGAAC CTGGACCCGG      120

AACTCATCAA GCAACTGGTG CCCGGAACGC TGGATCGGGC TTCGATCAAC GAGCAATTCG      180

CGGCCCTGAA GAAGGCGATA TTCGAGCGCG CGCTGGGCGG CGAACTGACC CACCACCTGG      240

GCTACGAGAA GGGCGATGCC AAGCCGGCGG GCCGCACGAA CCATCGCAAC GGCACCAGCC      300

GTAAGCGCAT CGCGACCGAC GATGATCTGC TCGACATCGA GATTCCGCGC GACCGCGAAG      360

GCACGTTCGA TCCGGTGCTG ATTGCCAAGG GCGAGCGACG CTTCACGGGC TTCGACGACA      420

AGATCATTGC GATGTACGCA CGCGGCATGA GCGTGCGGGA GATTCAGGGT TTCTTGCTGG      480

AGATGTACGG CATCGAGGTG TCGCCGGAAT TCATCAGCAC GGTGACCGAC GCCGTGATCG      540

ACGAAGTGCG CGAGTGGCAG CAGCGGCCGC TTGAGCCGAT GTACCCGGTC GTGTTCTTCG      600

ACGCCTTGCG AGTCAAGATC CGCGACGAAG GCGTCGTGCG CAACAAGGCG ATCTACCTGG      660

CGCTGGGCGT GCGCCGCGAC GGCACACGCG ACGTGCTGGG CCTCTGGATC GAGCAGACCG      720

AGGGCGCCAA GTTCTGGCTG CGGGTGGTCA ACGAGCTGAA GCTGCGCGGC GTGCAGGACA      780

TTCTGATCGC CGTGGTCGAC GGCCTGAAGG GCTTCCCGGA AGCGATCAAC ACGGTGTTCC      840

CGGAAACGAC GGTCCAGACC TGCATCGTGC ATCTGATCCG GAACTCGCTG GACTTCGCCA      900

GTTGGAAGGA CCGGAAATCG GTCGCGGCGG CGCTCAAGGA AGTCTATCGG GCACCGTCGG      960

CCGAAGCGGC CGCCGTGGCG CTGGACGCGT TCGATACGAG CCCGTGGGGT ACGAAATACC     1020

CTCCGATTGC CGCGCTCTGG CGCCGGGCCT GGGATCAGGT GATTCCGTTC TACGCCTTCG     1080

CGCCCGACAT CCGGAAAATT GTATATACGA CCAACGCGAT CGAGTCGCTG CATATGCAGC     1140

TTCGAAAGAT CATCAAGGCG CGCGGCCACT TCCCGTCGGA CGAGGCCGCG CTCAAACTGA     1200

TCTGGCTGGC GCTGCGCAAC GTCGTGGCCA AGTGGACCGG CTCTCGGCAC GATTGGAAGA     1260

GCGCGATGAC CCAGTTCGCG CTGCTTTACC CCGAACGATT CAACATTGGA ATCTGAATCT     1320

CAACCCGCCT CACACACGGA ATTCCGGATA CCT                                  1353
```

(2) INFORMATION FOR SEQ ID NO: 4:

(i) SEQUENCE CHARACTERISTICS:
        (A) LENGTH: 419 amino acids (B) TYPE: amino acid
(C) STRANDEDNESS: unknown
(D) TOPOLOGY: linear (ii) MOLECULE TYPE: protein (v) FRAGMENT TYPE: N-terminal (vi) ORIGINAL SOURCE:
(A) ORGANISM: Burkholderia cepacia
(C) INDIVIDUAL ISOLATE: ET12/cblA (xi) SEQUENCE DESCRIPTION: SEQ ID NO: 4:

```
Met Pro Arg Lys Arg Lys Glu Glu Val Pro Val Glu Pro Gly Lys Gly
1               5                   10                  15

Leu Asn Leu Asp Pro Glu Leu Ile Lys Gln Leu Val Pro Gly Thr Leu
            20                  25                  30

Asp Arg Ala Ser Ile Asn Glu Gln Phe Ala Ala Leu Lys Lys Ala Ile
            35                  40                  45

Phe Glu Arg Ala Leu Gly Gly Glu Leu Thr His His Leu Gly Tyr Glu
    50                  55                  60

Lys Gly Asp Ala Lys Pro Ala Gly Arg Thr Asn His Arg Asn Gly Thr
65                  70                  75                  80

Ser Arg Lys Arg Ile Ala Thr Asp Asp Leu Leu Asp Ile Glu Ile
                85                  90                  95

Pro Arg Asp Arg Glu Gly Thr Phe Asp Pro Val Leu Ile Ala Lys Gly
                100                 105                 110

Glu Arg Arg Phe Thr Gly Phe Asp Asp Lys Ile Ile Ala Met Tyr Ala
                115                 120                 125

Arg Gly Met Ser Val Arg Glu Ile Gln Gly Phe Leu Leu Glu Met Tyr
            130                 135                 140

Gly Ile Glu Val Ser Pro Glu Phe Ile Ser Thr Val Thr Asp Ala Val
145                 150                 155                 160

Ile Asp Glu Val Arg Glu Trp Gln Gln Arg Pro Leu Glu Pro Met Tyr
                165                 170                 175

Pro Val Val Phe Phe Asp Ala Leu Arg Val Lys Ile Arg Asp Glu Gly
                180                 185                 190

Val Val Arg Asn Lys Ala Ile Tyr Leu Ala Leu Gly Val Arg Arg Asp
            195                 200                 205

Gly Thr Arg Asp Val Leu Gly Leu Trp Ile Glu Gln Thr Glu Gly Ala
210                 215                 220

Lys Phe Trp Leu Arg Val Val Asn Glu Leu Lys Leu Arg Gly Val Gln
225                 230                 235                 240

Asp Ile Leu Ile Ala Val Val Asp Gly Leu Lys Gly Phe Pro Glu Ala
                245                 250                 255

Ile Asn Thr Val Phe Pro Glu Thr Thr Val Gln Thr Cys Ile Val His
                260                 265                 270

Leu Ile Arg Asn Ser Leu Asp Phe Ala Ser Trp Lys Asp Arg Lys Ser
    275                 280                 285

Val Ala Ala Leu Lys Glu Val Tyr Arg Ala Pro Ser Ala Glu Ala
    290                 295                 300

Ala Ala Val Ala Leu Asp Ala Phe Asp Thr Ser Pro Trp Gly Thr Lys
305                 310                 315                 320

Tyr Pro Pro Ile Ala Ala Leu Trp Arg Arg Ala Trp Asp Gln Val Ile
                325                 330                 335

Pro Phe Tyr Ala Phe Ala Pro Asp Ile Arg Lys Ile Val Tyr Thr Thr
                340                 345                 350
```

```
Asn Ala Ile Glu Ser Leu His Met Gln Leu Arg Lys Ile Ile Lys Ala
        355                 360                 365

Arg Gly His Phe Pro Ser Asp Glu Ala Ala Leu Lys Leu Ile Trp Leu
370                     375                 380

Ala Leu Arg Asn Val Val Ala Lys Trp Thr Gly Ser Arg His Asp Trp
385                 390                 395                 400

Lys Ser Ala Met Thr Gln Phe Ala Leu Leu Tyr Pro Glu Arg Phe Asn
                405                 410                 415

Ile Gly Ile
```

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 5:

```
GGCCCTGAAG AAGGCGATAT                                           20
```

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 6:

```
TCCGGCGACA CCTCGATGCC                                           20
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 7:

```
CAACCGAGAC TGAGGAGATG                                           20
```

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 8:

GCTGCTTGCC AATCGCGCTC                                               20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 9:

GACGGTGGGT CTGACGCCAT                                               20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Burkholderia cepacia
        (C) INDIVIDUAL ISOLATE: ET12/cblA (xi) SEQUENCE DESCRIPTION: SEQ ID NO: 10:

AAGCCCTGAG TCCCTCGTCG                                               20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Burholderia cepacia
        (C) INDIVIDUAL ISOLATE: ET12/cblA (xi) SEQUENCE DESCRIPTION: SEQ ID NO: 11:

TCATCGGGTT TCTGAAGGAA                                               20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
   (A) ORGANISM: Burholderia cepacia
   (C) INDIVIDUAL ISOLATE: ET12/cblA (xi) SEQUENCE DESCRIPTION: SEQ ID NO: 12:

CGGAAGCGAG CTGCACGGTC                                             20

(2) INFORMATION FOR SEQ ID NO: 13:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Burkholderia cepacia
      (C) INDIVIDUAL ISOLATE: ET12/cblA (xi) SEQUENCE DESCRIPTION: SEQ ID NO: 13:

TTGAAGGAAG TCCTGCGACT                                             20

(2) INFORMATION FOR SEQ ID NO: 14:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Burkholderia cepacia
      (C) INDIVIDUAL ISOLATE: ET12/cblA (xi) SEQUENCE DESCRIPTION: SEQ ID NO: 14:

TCGACTTCGC CCAATCCTTG                                             20

(2) INFORMATION FOR SEQ ID NO: 15:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Burkholderia cepacia
      (C) INDIVIDUAL ISOLATE: ET12/cblA (xi) SEQUENCE DESCRIPTION: SEQ ID NO: 15:

CCAAAGGACT AACCCA                                                 16

(2) INFORMATION FOR SEQ ID NO: 16:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Burkholderia cepacia

-continued (C) INDIVIDUAL ISOLATE: ET12/cblA (xi) SEQUENCE DESCRIPTION: SEQ ID NO: 16:

ACGCGATGTC CATCACA                                                                  17